(12) United States Patent
Kim et al.

(10) Patent No.: US 8,268,366 B2
(45) Date of Patent: Sep. 18, 2012

(54) COSMETIC COMPOSITION CONTAINING SALT-FERMENTED EXTRACT OF NATURAL MATERIALS

(75) Inventors: Dong Hyun Kim, Uiwang-si (KR); Jun Seong Park, Suwon-si (KR); Hye Yoon Park, Anyang-si (KR); Soo Mi Ahn, Suwon-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 62 days.

(21) Appl. No.: 13/056,931

(22) PCT Filed: May 7, 2009

(86) PCT No.: PCT/KR2009/002396
§ 371 (c)(1),
(2), (4) Date: Jan. 31, 2011

(87) PCT Pub. No.: WO2010/013885
PCT Pub. Date: Feb. 4, 2010

(65) Prior Publication Data
US 2011/0142972 A1    Jun. 16, 2011

(30) Foreign Application Priority Data
Aug. 1, 2008 (KR) .................. 10-2008-0075489
Apr. 22, 2009 (KR) .................. 10-2009-0034997

(51) Int. Cl.
*A01N 65/00*    (2009.01)

(52) U.S. Cl. ........................................ 424/725
(58) Field of Classification Search .............. None
See application file for complete search history.

(56) References Cited

FOREIGN PATENT DOCUMENTS

| KR | 10-2000-281011 | 11/2000 |
|---|---|---|
| KR | 10-2002-42084 | 6/2002 |
| KR | 10-2005-106710 | 11/2005 |
| KR | 10-2006-635782 | 10/2006 |
| KR | 10-2007-67542 | 6/2007 |
| KR | 2008022005 | * 3/2008 |
| WO | WO 01-74326 | 10/2001 |
| WO | WO 02-49656 | 6/2002 |

OTHER PUBLICATIONS

International Search Report for PCT/KR2009/002396, mailed Dec. 28, 2009.
Written Opinion of the International Searching Authority for PCT/KR2009/002396, mailed Dec. 28, 2009.

* cited by examiner

*Primary Examiner* — Michael Meller
(74) *Attorney, Agent, or Firm* — Nixon & Vanderhye P.C.

(57) ABSTRACT

The present invention relates to a cosmetic composition containing a fermented extract of natural material. More specifically, the present invention discloses a cosmetic composition that contains either a salt-fermented extract of at least one of red bean, mung bean and black bean or a salt-fermented extract of a mixture obtained by adding deep-sea water to at least one of red bean, mung bean and black bean, and thus has antioxidant and anti-aging effects.

1 Claim, No Drawings

COSMETIC COMPOSITION CONTAINING SALT-FERMENTED EXTRACT OF NATURAL MATERIALS

This application is the U.S. national phase of International Application No. PCT/KR2009/002396, filed 7 May 2009, which designated the U.S. and claims priority to KR Application No. 10-2008-0075489, filed 1 Aug. 2008, and KR Application No. 10-2009-0034997, filed 22 Apr. 2009, the entire contents of each of which are hereby incorporated by reference.

TECHNICAL FIELD

The present invention relates to a cosmetic composition containing a fermented extract of natural material, and more particularly to a cosmetic composition, that contains either a salt-fermented extract of at least one of red bean, mung bean and black bean or a salt-fermented extract of a mixture obtained by adding deep-sea water to at least one of red bean, mung bean and black bean, and thus has antioxidant and anti-aging effects.

BACKGROUND ART

Human skin undergoes changes with age due to a variety of internal and external factors. Specifically, with respect to the internal factors, the secretion of various hormones that regulate metabolism is reduced, the function of immunocytes and the activity of cells decline, and thus the biosynthesis of immune proteins and structural proteins that constitute a living body is reduced. With respect to the external factors, the amount of ultraviolet rays reaching the earth s surface is increasing due to destruction of the ozone layer, and as environmental pollution becomes ever more serious, free radicals and reactive oxygen species increase. As a result, skin thickness decreases, wrinkles increase, skin elasticity decreases, the skin color becomes darker, skin troubles frequently arise, and age spots, freckles and dark spots also increase.

As aging progresses, the content and arrangement of collagen, elastin, hyaluronic acid and glycoprotein that constitute the skin are changed or decrease, and oxidative stress occurs due to free radicals and reactive oxygen species. Also, it is known that, as aging progresses or by the action of UV rays, in most cells of the skin, the biosynthesis of cyclooxygenase-2 (Cox-2) producing proinflammatory cytokines known to cause inflammation increases, the biosynthesis of matrix metalloproteinase (MMP), which degrades skin tissue, increases due to these inflammatory factors, and the production of nitric oxide (NO) by inducible nitric oxide synthase (iNOS) increases. That is, due to intrinsic aging that naturally progresses, the activity of cells is reduced, and the biosynthesis of substrates is reduced due to minute inflammation. In addition, due to external factors such as an increase in stress caused by various harmful pollutants and an increase in reactive oxygen species caused by the sunlight, degradation and denaturation are accelerated, and thus the skin matrix is broken and becomes thinner, while various symptoms of skin aging appear. For this reason, many studies on active ingredients that can prevent and ameliorate such aging phenomena are being conducted.

Meanwhile, it is known that reactive oxygen species that are produced by various physical, chemical and environmental factors, including an in vivo enzyme system, reductive metabolism, chemicals, pollutants and a photochemical reaction, cause cell aging and various diseases including cancer by showing a non-selective, non-reversible destructive reaction against cell components such as lipid, protein, sugar and DNA. In addition, a variety of in vivo peroxides, including lipid peroxides, that are produced as a result of lipid peroxidation caused by these reactive species also cause oxidative destruction against cells to cause various functional disorders, thus causing various diseases. Accordingly, antioxidants such as free radical scavengers capable of eliminating such free radicals and peroxide inhibitors can be used as agents for inhibiting or treating aging and various diseases resulting from such oxides.

As a result of recent well-being health trends, demand for fermenting natural materials using a natural fermentation method without using artificial factors has increased, and demand for products manufactured using the fermented natural materials continues to increase. However, due to the risk of decomposition and contamination by *E. coli* bacteria and anaerobic bacteria that are harmful to the human body, it is difficult to use such natural fermentation methods to manufacture actual products. To solve this problem, a method of carrying out sterilization before fermentation, such as a boiling method, was devised, however effective components can be degraded by heat. For this reason, the need to develop a fermentation method that uses a non-sterilization method exists.

DISCLOSURE OF INVENTION

Technical Problem

Accordingly, the present inventors have conducted studies to prepare an antioxidant and anti-aging cosmetic composition, that contains an active ingredient derived from natural material, is safe for the skin and has excellent antioxidant and anti-aging effects and excellent product stability. As a result, the present inventors have found that a salt-fermented extract prepared through a natural fermentation method of fermenting natural materials after salting the materials has excellent antioxidant and anti-aging effects, thereby completing the present invention.

An object of the present invention is therefore to provide a cosmetic composition that contains a salt-fermented extract of natural material, and thus has excellent skin antioxidant and anti-aging effects.

Technical Solution

The cosmetic composition that is provided by the present invention contains, as an active ingredient, a salt-fermented extract of at least one selected from the group consisting of red bean, mung bean and black bean. Alternatively, the cosmetic composition of the present invention may contain, as an active ingredient, a salt-fermented extract of a mixture obtained by adding deep-sea water to at least one selected from the group consisting of red bean, mung bean and black bean. The cosmetic composition of the present invention contains, as an active ingredient, the salt-fermented extract in an amount of 0.0001-30 wt % based on the total weight of the composition. If the content of the salt-fermented extract is less than 0.0001 wt %, the antioxidant and anti-aging effects of the extract cannot be obtained, and if the content exceeds 30 wt %, the increase in the content does not provide a significant increase in the effects.

The red bean used in the present invention is generally called Pat in Korean, and has diuretic, anti-inflammatory, wound-draining and fever-alleviating effects and is used for generalized edema, liver cirrhosis, jaundice, swelling, suppurative disease, dropsy, beriberi, diseases symptomized by thirst, dysenteric diarrhea and the like.

The mung bean used in the present invention is called Andu or Gildu in Korean. The mung bean grows well in soil in a warm climate and is 30-80 cm in height. The stem has thin and vertical veins and about 10 knots and spreads into branches. With respect to the leaf, a pair of seed leaves, and other fresh leaves, come out, and then a compound leaf consisting of three small leaves comes out. The mung bean is classified, according to the color of the seed, into yellow mung bean, greenish brown mung bean and blackish brown mung bean, wherein green mung bean accounts for 90% of the total mung beans. It contains 53-54% starch and 25-26% protein, is highly nutritious and has a good flavor. It is used to treat skin disease in folk remedies and is known to have fever-alleviating and poison-neutralizing effects.

The black bean used in the present invention is called Komjung kong or Heuk-dae-doo in Korean. The names collectively designate blackish beans rather than designating a certain kind of bean. Heuk-tae, Seo-ri-tae and Seo-mok-tae in Korean are specific kinds of black bean. It is known that black bean has a nutrient content similar to that of general beans, but contains anti-aging ingredients in an amount four times larger than those of general beans and has effects of preventing adult diseases and promoting weight loss. The Bon-cho-gang-mok (Chinese medicinal plant book) records that black bean has effects of regulating the kidneys, removing edema, activating blood circulation and neutralizing the poison of all drugs. Also, it is known that black bean contains cystein essential for hair growth, and thus has the effect of preventing hair loss. In addition, black bean is known to make the function of kidneys and bladder smooth when continuously administered.

Deep-sea water used in the present invention is found in deep sea areas having a depth of greater than 200 m, and has few or no organisms or pathogenic bacteria. The deep-sea water is stably maintained at low temperature throughout the year, and is rich in nutrient salts essential for the growth of marine plants and has a good mineral balance.

Salt-fermented extracts of red bean, mung bean and black bean that are used in the present invention are prepared in the following manner.

Step 1: Fermentation of Red Bean, Mung Bean and Black Bean

First, a predetermined amount of salt is added to red bean, mung bean or black bean, and the salted bean is aged and fermented for an extended period of time. Alternatively, deep-sea water together with salt may be added to the bean, and then the bean may be salt-fermented. For an amount of 1 kg of red bean, mung bean or black bean, deep-sea water is preferably added in an amount of 1-2 l.

Preferred examples of salt used in the salting process include high-purity sodium chloride, solar salt, rock salt and bamboo salt, and the concentration of salt is preferably 10-30 wt % based on the total weight of the fermented material. If the content of salt is less than 10 wt %, it is difficult to obtain the desired salting effect, and if the content exceeds 30 wt %, the increase in the amount of salt used does not provide a significant increase in the salting effect.

The fermentation process in the present invention may be performed at a temperature between 4 and 40° C. for a period ranging from 30 days to 1 year, and preferably from 6 months to 1 year, such that sufficient fermentation can occur.

Step 2: Collection of Salt-fermented Extract

A salt-fermented extract is collected from the salt-fermented natural material of step 1 using an extraction solvent.

The extraction solvent used in the present invention may be water or an organic solvent, and preferably one, or a mixture of at least two, selected from the group consisting of purified water, methanol, ethanol, glycerin, ethyl acetate, butylene glycol, propylene glycol, dichloromethane and hexane.

The extraction temperature is preferably between 10 and 80° C., and the extraction process is performed for 6-24 hours. If the extraction temperature or extraction time are outside of the above-specified ranges, the extraction efficiency can be reduced or the components of the extract can be changed.

After obtaining the extract using the solvent, a liquid-phase material can be obtained by performing cold-water extraction at room temperature, heating and filtration according to a conventional method known in the art. Alternatively, solvent evaporation, spray drying or freeze drying may additionally be carried out, thus preparing a salt-fermented extract of red bean, mung bean or black bean or a salt-fermented extract of a mixture obtained by adding deep-sea water to red bean, mung bean or black bean.

It can be confirmed through a test of inhibition of DPPH oxidation that a cosmetic composition containing the salt-fermented extract prepared using the above-described method has antioxidant effects. Also, the cosmetic composition has the effects of promoting procollagen production and inhibiting collagenase expression and can show an excellent effect of reducing skin wrinkling due to the synergistic effect of the two activities.

The salt-fermented extract according to the present invention is not limited to any particular application and may be used in, for example, health food additives and pharmaceutical compositions in addition to cosmetic compositions.

Advantageous Effects

It was confirmed through a test of inhibition of DPPH oxidation that a salt-fermented extract of red bean, mung bean or black bean according to the present invention has antioxidant effects. Also, the salt-fermented extract showed the effects of promoting pro-collagen production and inhibiting collagenase expression and can provide an excellent effect of reducing skin wrinkling due to the synergistic effect of the two activities.

BEST MODE FOR CARRYING OUT THE INVENTION

Hereinafter, the present invention is described in further detail with reference to examples and test examples, however the scope of the present invention is not limited only to these examples.

EXAMPLE 1

Preparation of Salt-fermented Extract of Red Bean, Mung Bean, Black Bean and Deep-sea Water 1 kg of each of washed red bean, mung bean and black bean together with 1 l of deep-sea water were mixed with a salt solution having a salt concentration of 10 wt % and placed in a pot. Then, the mixture was stored and aged in a light-shielded dark room at 4° C. for about 30 days. Subsequently, 5 l of an 80% ethanol aqueous solution was added thereto, and the resulting solution was extracted three times under reflux, and then incubated at 15° C. for 1 day. The solution was filtered through filter cloth and centrifuged into a residue and a filtrate, and the separated filtrate was concentrated under reduced pressure. The concentrated filtrate was suspended in water, the suspension was extracted five times with 1 l of ether to remove pigments, and the aqueous layer was extracted three times with 500 ml of 1-butanol. The resulting total 1-butanol layer was concentrated under reduced pressure to obtain a 1-butanol extract, which was then dissolved in a small amount of methanol. The solution was added to a large amount of ethyl acetate, and the produced precipitate was dried, thus obtaining 190 g of a salt-fermented extract of red bean, mung bean, black bean and deep-sea water.

EXAMPLE 2

Preparation of Salt-fermented Extract of Red Bean and Deep-sea Water 1 kg of dried red bean with 1 l of deep-sea water was treated in the same manner as described in Example 1, thus obtaining 182 g of a salt-fermented extract of red bean and deep-sea water.

EXAMPLE 3

Preparation of Salt-fermented Extract of Mung Bean and Deep-sea Water 1 kg of dried mung bean with 1 l of deep-sea water was treated in the same manner as described in Example 1, thus obtaining 172 g of a salt-fermented extract of mung bean and deep-sea water.

EXAMPLE 4

Preparation of Salt-fermented Extract of Black Bean and Deep-Sea Water 1 kg of dried black bean with 1 l of deep-sea water was treated in the same manner as described in Example 1, thus obtaining 178 g of a salt-fermented extract of black bean and deep-sea water.

EXAMPLE 5

Preparation of Salt-fermented Extract of Red Bean 1 kg of dried red bean was treated in the same manner as described in Example 1, except that deep-sea water was not added, thus obtaining 210 g of a salt-fermented extract of red bean.

EXAMPLE 6

Preparation of Salt-fermented Extract of Mung Bean 1 kg of dried mung bean was treated in the same manner as described in Example 1, except that deep-sea water was not added, thus obtaining 193 g of a salt-fermented extract of mung bean.

EXAMPLE 7

Preparation of Salt-fermented Extract of Black Bean 1 kg of dried black bean was treated in the same manner as described in Example 1, except that deep-sea water was not added, thus obtaining 198 g of a salt-fermented extract of black bean.

COMPARATIVE EXAMPLE 1

Preparation of Fermented Extract of Red Bean, Mung Bean, Black Bean and Deep-sea Water 1 kg of each of washed red bean, mung bean and black bean together with 1 l of deep-sea water and placed in a pot. Then, the mixture was stored and aged in a light-shielded dark room at 4° C. for about 30 days. Subsequently, 5 l of an 80% ethanol aqueous solution was added thereto, and the resulting solution was extracted three times under reflux, and then incubated at 15° C. for 1 day. The solution was filtered through filter cloth and centrifuged into a residue and a filtrate, and the separated filtrate was concentrated under reduced pressure. The concentrated filtrate was suspended in water, the suspension was extracted five times with 1 l of ether to remove pigments, and the aqueous layer was extracted three times with 500 ml of 1-butanol. The resulting total 1-butanol layer was concentrated under reduced pressure to obtain a 1-butanol extract, which was then dissolved in a small amount of methanol. The solution was added to a large amount of ethyl acetate, and the produced precipitate was dried, thus obtaining 185 g of a fermented extract of red bean, mung bean, black bean and deep-sea water.

COMPARATIVE EXAMPLE 2

Preparation of Extract of Red Bean, Mung Bean, Black Bean and Deep-sea Water 1 kg of each of washed red bean, mung bean and black bean was mixed with 1 l of deep-sea water, then 5 l of an 80% ethanol aqueous solution was added thereto, and the resulting solution was extracted three times under reflux, and then incubated at 15° C. for 1 day. The solution was filtered through filter cloth and centrifuged into a residue and a filtrate, and the separated filtrate was concentrated under reduced pressure. The concentrated filtrate was suspended in water, the suspension was extracted five times with 1 l of ether to remove pigments, and the aqueous layer was extracted three times with 500 me of 1-butanol. The resulting total 1-butanol layer was concentrated under reduced pressure to obtain a 1-butanol extract, which was then dissolved in a small amount of methanol. The solution was added to a large amount of ethyl acetate, and the produced precipitate was dried, thus obtaining 170 g of an extract of red bean, mung bean, black bean and deep-sea water.

TEST EXAMPLE 1

Test of Antioxidant Effect (DPPH Test)

The DPPH oxidation inhibitory effect of the extracts of natural materials obtained in Comparative Examples 1 and 2 and the salt-fermented extracts of natural materials obtained in Examples 1 to 7 were measured comparatively with that of Trolox, a widely used synthetic antioxidant.

In the measurement, the antioxidant activity of the extracts were evaluated by measuring the change in absorbance resulting from a reduction of the organic radical DPPH (1,1-diphenyl-2-picryl hydrazyl) due to oxidization of the antioxidant. The degree to which absorbance was reduced due to the inhibition of DPPH oxidation by the extracts obtained in Comparative Examples 1 and 2 and Examples 1 to 7 was measured and compared to that of a control group, and a concentration showing an absorbance 50% lower than the absorbance of the control group was evaluated as an effective antioxidant concentration.

190 μl of a 100 μM DPPH solution in ethanol was mixed with 10 μl of each of a control sample and the extracts obtained in the Examples and Comparative Examples to prepare reaction solutions. Each reaction solution was allowed to react at 37° C. for 30 minutes and measured for absorbance at 540 nm. As the control sample, Trolox, a widely used synthetic antioxidant, was used. The results of DPPH analysis for each material are shown in Table 1 below. In Table 1, $IC_{50}$ indicates the sample concentration at which absorbance was reduced by 50% due to the added sample.

TABLE 1

DPPH analysis results (inhibition %)

| Samples | | $IC_{50}$ (ppm) |
|---|---|---|
| Trolox | | 45 |
| Comparative Example 1 | Fermented extract of red bean + mung bean + black bean + deep sea water | 183 |
| Comparative Example 2 | Extract of red bean + mung bean + black bean + deep sea water | 145 |
| Example 1 | Salt-fermented extract of red bean + mung bean + black bean + deep sea water | 39 |
| Example 2 | Salt-fermented extract of red bean + deep sea water | 51 |
| Example 3 | Salt-fermented extract of mung bean + deep sea water | 46 |
| Example 4 | Salt-fermented extract of black bean + deep sea water | 49 |
| Example 5 | Salt-fermented extract of red bean | 89 |
| Example 6 | Salt-fermented extract of mung bean | 95 |
| Example 7 | Salt-fermented extract of black bean | 87 |

As can be seen in Table 1, the salt-fermented extracts of red bean, mung bean and/or black bean, prepared in Examples 1 to 7 of the present invention, had a significantly greater antioxidant effect compared to that of the fermented extract of Comparative Example 1 and the simple extract of Comparative Example 2.

Further, it can be seen that the salt-fermented extracts of the mixtures obtained by adding salt and deep-sea water to red bean, mung bean or black bean, prepared in Examples 2 to 4, showed an excellent antioxidant effect compared to that of the simple salt-fermented extracts of the mixtures comprising red bean, mung bean or black bean without deep-sea water, prepared in Examples 5 to 7.

Further, it can be seen that the extracts of Examples 2 to 4 showed an antioxidant activity similar to that of the synthetic antioxidant Trolox, but the salt-fermented extract of the mixture of red bean, mung bean, black bean and deep-sea water, prepared in Example 1, showed an excellent antioxidant activity compared to that of Trolox.

TEST EXAMPLE 2

Measurement of Collagenase Expression Inhibitory Activity

The collagenase expression inhibitory activity of the extracts of natural materials, prepared in Comparative Examples 1 and 2, and the salt-fermented extracts of natural materials, prepared in Examples 1 to 7, were measured comparatively with those of tocopherol and EGCG. If the collagenase expression inhibitory activity is high, the expression level of collagen is low, less degradation of collagen in the skin occurs, and thus the amount of wrinkling produced is also reduced. Tocopherol and EGCG, which are antioxidant substances, are known to prevent skin aging by regenerating the epidermal cells of the skin.

In the test, human fibroblasts were seeded into a 96-well microtiter plate containing DMEM (Dulbecco's Modified Eagle's Media) medium containing 2.5% fetal bovine serum to a density of 5,000 cells/well and were cultured to a confluence of about 90%. Then, the cells were cultured in serum-free DMEM medium for 24 hours and treated with the extracts of Comparative Examples 1 and 2 and Examples 1 to 7, tocopherol and EGCG, dissolved in serum-free DMEM medium, at a concentration of $10^{-4}$ mole for 24 hours. The cell culture broths were then collected.

The collected cell culture broths were measured for collagenase production using a commercially available collagenase measurement device (Amersham Phamasia, USA). First, the collected cell culture broths were placed into a 96-well plate containing primary collagenase antibody applied uniformly thereto and were subjected to an antigen-antibody reaction in a constant-temperature bath for 3 hours.

After 3 hours, chromophore-conjugated secondary collagen antibody was placed into the 96-well plate and allowed to react for 15 minutes. After 15 minutes, a substance inducing color development was added to the 96-well plate, and color development was induced at room temperature for 15 minutes. When 1 M sulfuric acid was added to the 96-well plate to stop the (color development reation), the reaction solution had a yellow color, and the intensity of the yellow color varied depending on the degree of progression of the reaction.

The absorbance of the 96-well plate having a yellow color was measured at 405 nm using an absorbance spectrometer, and the degree of synthesis of collagenase was calculated according to the following Equation 1. Herein, the absorbance of the cell culture broth collected from the group not treated with the composition was used as a control. That is, the expression of collagenase in the control group was set as 100, and the expression of collagenase in the group treated with the composition was calculated relative to the control group. The calculation results are shown in Table 2 below.

MathFigure 1

$$\text{Collagenase exprexssion (\%)} = \frac{\text{absorbance of cell group treat with material}}{\text{absorbance of control group}} \times 100 \quad \text{[Math. 1]}$$

TABLE 2

| Materials | | Collagenase expression (%) |
|---|---|---|
| Control group | | 100 |
| Tocopherol | | 75 |
| EGCG | | 60 |
| Comparative Example 1 | Fermented extract of red bean + mung bean + black bean + deep sea water | 136 |
| Comparative Example 2 | Extract of red bean + mung bean + black bean + deep sea water | 112 |
| Example 1 | Salt-fermented extract of red bean + mung bean + black bean + deep sea water | 66 |
| Example 2 | Salt-fermented extract of red bean + deep sea water | 76 |
| Example 3 | Salt-fermented extract of mung bean + deep sea water | 79 |

TABLE 2-continued

| Materials | | Collagenase expression (%) |
|---|---|---|
| Control group | | 100 |
| Tocopherol | | 75 |
| EGCG | | 60 |
| Example 4 | Salt-fermented extract of black bean + deep sea water | 82 |
| Example 5 | Salt-fermented extract of red bean | 90 |
| Example 6 | Salt-fermented extract of mung bean | 94 |
| Example 7 | Salt-fermented extract of black bean | 97 |

As can be seen in Table 2 above, the fermented extract of Comparative Example 1 and the simple extract of Comparative Example 2 did not inhibit collagenase expression compared to the control group, and thus had no collagenase expression inhibitory activity.

However, it can be seen that the salt-fermented extracts of red bean, mung bean and black bean, prepared in Examples 1 to 7 of the present invention, all inhibited the expression of collagenase in vitro, although they showed differences between each other with respect to the degree of collagenase expression.

Also, it can be seen that the salt-fermented extracts of the mixtures of red bean, mung bean or black bean with deep-sea water, prepared in Examples 1 to 4, had a significantly greater collagenase inhibitory activity compared to that of the simple salt-fermented extracts prepared in Examples 5 to 7, and the collagenase expression inhibitory activity of Examples 1 to 4 was excellent compared to that of tocopherol known as an antioxidant substance.

TEST EXAMPLE 3

Test of the Effect of Promoting Procollagen Production

The procollagen production ability of the extracts of natural materials, prepared in Comparative Examples 1 and 2, and the salt-fermented extracts of natural materials, prepared in Examples 1 to 7, were measured comparatively with that of vitamin C. Procollagen is a collagen production-inducing substance necessary for collagen production and aging prevention, and if the degree of production of procollagen is high, the degree of production of collagen is also high, and thus the production of skin wrinkles can be prevented. Also, vitamin C is known as a component essential for the synthesis of collagen.

In the test, human fibroblasts were seeded into a 96-well microtiter plate containing DMEM (Dulbecco's Modified Eagle's Media) medium containing 2.5% fetal bovine serum to a density of 5,000 cells/well and were cultured to a confluence of about 90%. Then, the cells were cultured in serum-free DMEM medium for 24 hours and treated with the extracts of Comparative Examples 1 and 2 and Examples 1 to 7 and vitamin C, dissolved in serum-free DMEM medium, at a concentration of $10^{-4}$ mole for 24 hours. The cell culture broths were then collected. After 24 hours, the amount of released procollagen in the medium was measured with a procollagen type-1 C-peptide EIA kit (MK101, Takara, Japan).

Based on the measurement results, the production of procollagen was calculated according to the following Equation 2. Herein, the production of procollagen collected from the group not treated with the composition was used as a control group. That is, the production of procollagen in the control group was set as 100, and the production of procollagen in the groups treated with the composition was calculated relative to the control group. The calculation results are shown in Table 3 below.

MathFigure 2

$$\text{Procollagen production (\%)} = \frac{\text{procollagen production in group treated with material}}{\text{procollagen production in control group}} \times 100 \qquad [\text{Math. 2}]$$

TABLE 3

| Materials | | Procollagen production (%) |
|---|---|---|
| Control group | | 100 |
| Vitamin C | | 120 |
| Comparative Example 1 | Fermented extract of red bean + mung bean + black bean + deep sea water | 56 |
| Comparative Example 2 | Extract of red bean + mung bean + black bean + deep sea water | 86 |
| Example 1 | Salt-fermented extract of red bean + mung bean + black bean + deep sea water | 118 |
| Example 2 | Salt-fermented extract of red bean + deep sea water | 104 |
| Example 3 | Salt-fermented extract of mung bean + deep sea water | 108 |
| Example 4 | Salt-fermented extract of black bean + deep sea water | 105 |
| Example 5 | Salt-fermented extract of red bean | 101 |
| Example 6 | Salt-fermented extract of mung bean | 103 |
| Example 7 | Salt-fermented extract of black bean | 103 |

As can be seen in Table 3 above, the fermented extract of Comparative Example 1 and the simple extract of Comparative Example 2 did not promote the production of procollagen compared to the control group.

However, it can be seen that the salt-fermented extracts of red bean, mung bean and black bean, prepared in Examples 1 to 7 of the present invention, all promoted the production of procollagen in vitro, although they showed differences between each other with respect to the degree of promotion of procollagen production.

Also, it can be seen that the salt-fermented extracts of the mixtures obtained by adding deep-sea water to red bean, mung bean or black bean, prepared in Examples 1 to 4, had a significantly greater ability of promoting procollagen production compared to that of the simple salt-fermented extracts prepared in Examples 5 to 7, and the pro-collagen production-promoting ability of Examples 1 to 4 was similar to that of vitamin C known as a component essential for the synthesis of collagen.

Hereinafter, formulation examples of a composition containing a salt-fermented extract of a mixture obtained by adding deep-sea water to red bean, mung bean and black bean are described, however the cosmetic composition of the present invention is not limited only to these examples.

FORMULATION EXAMPLE 1

Lotion

A milk lotion containing the salt-fermented extract of a mixture obtained by adding deep-sea water to red bean, mung bean and black bean of Example 1 was prepared according to the composition shown in Table 4 below.

TABLE 4

| Components | Contents (wt %) |
|---|---|
| Example 1 | 5.0 |
| Squalane | 5.0 |
| Bees wax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment and perfume | q.s. |
| Purified water | Balance |
| Total | 100 |

FORMULATION EXAMPLE 2

Skin lotion

A skin lotion containing the salt-fermented extract of a mixture obtained by adding deep-sea water to red bean, mung bean and black bean of Example 1 was prepared according to the composition shown in Table 5 below.

TABLE 5

| Components | Contents (wt %) |
|---|---|
| Example 1 | 5.0 |
| Glycerin | 3.0 |
| Butylene glycol | 2.0 |
| Propylene glycol | 2.0 |
| Carboxyvinyl polymer | 0.1 |
| PEG 12 nonylphenylether | 0.2 |
| Polysorbate 80 | 0.4 |
| Ethanol | 10.0 |
| Triethanolamine | 0.1 |
| Preservative, pigment and perfume | q.s. |
| Purified water | Balance |
| Total | 100 |

FORMULATION EXAMPLE 3

Nourishing Cream

A nourishing cream containing the salt-fermented extract of a mixture obtained by adding deep-sea water to red bean, mung bean and black bean of Example 1 was prepared according to the composition shown in Table 6 below.

TABLE 6

| Components | Contents (wt %) |
|---|---|
| Example 1 | 5.0 |
| Polysorbate 60 | 1.5 |
| Sorbitan sesquioleate | 0.5 |
| PEG60 hydrogenated castor oil | 2.0 |
| Liquid paraffin | 10.0 |
| Squalane | 5.0 |
| Caprylic/capric triglyceride | 5.0 |
| Glycerin | 5.0 |

TABLE 6-continued

| Components | Contents (wt %) |
|---|---|
| Butylene glycol | 3.0 |
| Propylene glycol | 3.0 |
| Triethanolamine | 0.2 |
| Preservative, pigment and perfume | q.s. |
| Purified water | Balance |
| Total | 100 |

FORMULATION EXAMPLE 4

Massage Cream

A massage cream containing the salt-fermented extract of a mixture obtained by adding deep-sea water to red bean, mung bean and black bean of Example 1 was prepared according to the composition shown in Table 7 below.

TABLE 7

| Components | Contents (wt %) |
|---|---|
| Example 1 | 5.0 |
| Bees wax | 10.0 |
| Polysorbate 60 | 1.5 |
| Sorbitan sesquioleate | 0.8 |
| PEG60 hydrogenated castor oil | 2.0 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, pigment and perfume | q.s. |
| Purified water | Balance |
| Total | 100 |

FORMULATION EXAMPLE 5

Pack

A pack containing the salt-fermented extract of a mixture obtained by adding deep-sea water to red bean, mung bean and black bean of Example 1 was prepared according to the composition shown in Table 8 below.

TABLE 8

| Components | Contents (wt %) |
|---|---|
| Example 1 | 5.0 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG 12 nonylphenylether | 0.3 |
| Polysorbate 60 | 0.3 |
| Preservative, pigment and perfume | q.s. |
| Purified water | Balance |
| Total | 100 |

The invention claimed is:

1. A cosmetic composition consisting essentially of 0.0001-30 wt. % of deep sea water and 0.0001-30 wt. % of a salt fermented extract of at least one bean selected from the group consisting of red bean, mung bean, and black bean.

* * * * *